United States Patent [19]

Lumma, Jr. et al.

[11] 4,163,849

[45] Aug. 7, 1979

[54] PIPERAZINYLPYRAZINES

[75] Inventors: William C. Lumma, Jr., Pennsburg; Walfred S. Saari, Lansdale; Anthony G. Zacchei, Ambler, all of Pa.

[73] Assignee: Merck & Co., Inc., Rahway, N.J.

[21] Appl. No.: 887,693

[22] Filed: Mar. 17, 1978

[51] Int. Cl.² .................. A61K 31/495; C07D 403/04
[52] U.S. Cl. ..................................... 544/357; 424/250
[58] Field of Search .......................................... 544/357

[56] References Cited

U.S. PATENT DOCUMENTS

| 2,459,367 | 1/1949 | Denton et al. | 544/357 |
| 3,631,043 | 12/1971 | Regnier et al. | 544/357 |
| 4,081,542 | 3/1978 | Lumma et al. | 544/357 |
| 4,082,844 | 4/1978 | Lumma et al. | 544/357 |

FOREIGN PATENT DOCUMENTS 2617205  10/1976  Fed. Rep. of Germany.

Primary Examiner—Donald G. Daus
Assistant Examiner—James H. Turnipseed
Attorney, Agent, or Firm—Mario A. Monaco; Martin L. Katz

[57] ABSTRACT

Substituted piperazinylpyrazines and pharmaceutically acceptable salts thereof which have pharmacological activity as anorexigenic agents.

6 Claims, No Drawings

PIPERAZINYLPYRAZINES

BACKGROUND OF THE INVENTION

This invention is concerned with substituted piperazinylpyrazines and pharmaceutically acceptable salts thereof which demonstrate serotoninmimetic activity and hence are useful as anorexigenic, anti-depressant, analgesic and hypnotic agents, to a method of preparing these compounds, to pharmaceutical formulations containing these compounds, and to methods of administering these compounds to an animal or human.

Obesity is a fairly common condition and a potentially serious one in view of the correlation between incidence of various diseases and the degree to which a person is overweight. For example, obese persons succumb statistically more frequently to cardiovascular renal disease than do persons of normal weight. Obesity likewise results in higher death rates from diabetes, nephritis, pneumonia, cirrhosis, appendicitis and post-operative complications. Since obesity often occurs simply as a consequence of excessive intake of calories, good management of the condition in these cases can be achieved by restricting the caloric intake. Frequently, however, the patient has difficulty in initiating and maintaining dietary restrictions, making it necessary to employ anorexigenic drugs as adjuvants to therapy.

Accordingly, it is an object of the present invention to provide piperazinylpyrazines which are effective anorexigenic agents. Another object is to provide pharmaceutical formulations for the administration of these and other related anorexigenic agents. Further objects are to provide methods for preparing the piperazinylpyrazines and for administering piperazinylpyrazine anorexigenic agents to a mammalian animal or human.

DETAILED DESCRIPTION OF THE INVENTION

The novel compounds of this invention have the structural formula:

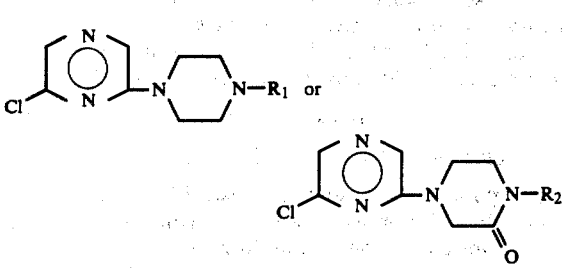

wherein $R_1$ is allyl; cycloalkyl such as cyclopropyl and cyclopropylalkyl of 4–6 carbon atoms; or propaniminooxycarbonyl and $R_2$ is alkyl of 1–4 carbon atoms and pharmaceutically acceptable salts thereof.

The most preferred compounds of this class are:
6-chloro-2-(4-allyl-1-piperazinyl)-pyrazine;
6-chloro-2-(4-cyclopropyl-1-piperazinyl)-pyrazine;
6-chloro-2-(4-cyclopropylmethyl-1-piperazinyl)-pyrazine;
6-chloro-2-[4-(2'-propaniminooxycarbonyl)-1-piperazinyl]-pyrazine; and
6-chloro-2-(4-methyl-3-oxo-1-piperazinyl)-pyrazine.

Also included within the scope of the present invention are non-toxic pharmaceutically acceptable salts. Such acid addition salts of the novel compound are formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, sulfuric acid, phosphoric acid, nitric acid, isethionic acid or the like.

These compounds may be prepared by a process in which a halo pyrazine is reacted with a substituted piperazine. This reaction may be represented by the following:

wherein X is chloro, bromo or iodo and R is alkyl. The reaction occurs at temperatures ranging from ambient to about 150° C. either neat or in an inert solvent such as benzene, toluene, xylene, acetonitrile, ethanol or butanol for a period of from about 0.5 to about 10 hours.

Alternatively the N-methyl compound may be prepared by alkylating the unsubstituted 3-oxo-piperazinylpyrazine with a suitable alkylating agent such as methyl iodide, methyl bromide, methyl tosylate or diazomethane. When using this procedure, the 3-oxo-piperazinylpyrazine is first reacted with a strong base such as sodium hydride, or an alkali metal alkoxide in an inert solvent such as tetrahydrofuran, dimethylsulfoxide, dimethylformamide, benzene, toluene, xyline, ethanol or butanol. The reaction is then completed by adding the alkylating agent and conducting the reaction at a temperature of from ambient to about 100° C. for a period of from 0.5 to 10 hours.

The other N-substituted piperazinylpyrazines may be prepared by reacting 6-chloro-2-(1-piperazinyl)-pyrazine with the appropriate reactant such as acetic anhydride, formic acetic anhydride, benzoyl chloride, 2-propaniminooxycarbonyl chloride, etc. either in an aqueous system containing a base such as an alkali metal hydride, carbonate, bicarbonate or acetate, or in an inert solvent such as benzene, toluene, pyridine, etc., at a temperature of from 0 to about 100° C. for a period of from 0.5 to 10 hours.

A further embodiment of this invention is a method of producing an anorexigenic effect in patients in need of such treatment that comprises administering a therapeutically effective amount of the compound or compositions of the formula:

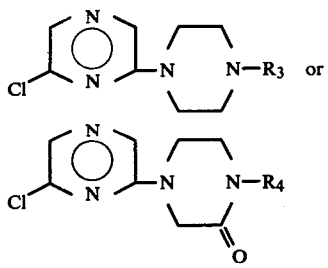

wherein R₃ is alkanoyl of 1-3 carbon atoms such as formyl or acetyl; aroyl such as benzoyl; alkyl of 1-4 carbon atoms such as methyl; allyl; propaniminooxycarbonyl; or cycloalkyl such as cyclopropyl and cyclopropylalkyl of 4-6 carbon atoms and R₄ is alkyl of 1-4 carbon atoms and pharmaceutically acceptable salts thereof.

The most preferred compounds of this class are:
6-chloro-2-(4-methyl-1-piperazinyl)-pyrazine;
6-chloro-2-(4-formyl-1-piperazinyl)-pyrazine;
6-chloro-2-(4-acetyl-1-piperazinyl)-pyrazine;
6-chloro-2-(4-allyl-1-piperazinyl)-pyrazine;
6-chloro-2-(4-cyclopropyl-1-piperazinyl)-pyrazine;
6-chloro-2-(4-cyclopropylmethyl-1-piperazinyl)-pyrazine; 6-chloro-2-[4-(2'1 -propaniminooxycarbonyl)-1-piperazinyl]-pyrazine; and
6-chloro-2-(4-methyl-3-oxo-1-piperazinyl)-pyrazine.

Typically the dosage level ranges from about 0.1 to about 100 mg/day of the active compounds of the present invention.

The compounds of this invention also find utility as antidepressant, analgesic and hypnotic agents and for such purposes are administered as described above. Pharmaceutical compositions comprising the novel compound as active ingredient may be in any art recognized form suitable for oral use, such as tablets, troches, lozenges, aqueous or oil suspensions, dispersible powders, or granule, emulsions, hard or soft capsules, syrups, or elixirs. For intravenous and intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from about 0.1 to about 100 mg.

The following examples illustrate the present invention without, however, limiting the same.

EXAMPLE 1

6-chloro-2-(3-oxo-1-piperazinyl)-pyrazine

A mixture of 10.0 g (0.0067 mole) of 2,6-dichloropyrazine and 14 g (0.14 mole) of 2-oxopiperazine in 100 ml of acetonitrile is refluxed 1.5 hour with stirring under N₂. The mixture is concentrated under vacuum, the residue titrated with water and filtered, and the crude solid recrystallized from water (charcoal treatment) to give off-white plates of the subject compound, 7.7 g, mp 192°-193° C.

EXAMPLE 2

6-chloro-2-(4-methyl-3-oxo-1-piperazinyl)-pyrazine

The product of Example 1 (2.13 g, 0.01 mole) and sodium hydride-oil suspension (50%, 0.50 g, 0.01 mole) are combined in 10 ml N,N-dimethylformamide and the stirred mixture treated with 0.65 ml (0.01 mole) of methyl iodide in 5 ml toluene. The mixture is stirred 1 hour at room temperature, diluted with water and extracted with toluene. The toluene extracts are washed with water, dried over sodium sulfate, filtered and concentrated in vacuo to give the crude product which is chromatographed on neutral (activity III) alumina. Elution with chloroform gives fractions containing 1.4 of a white solid which is recrystallized from n-butyl-chloride-cyclohexane to give white crystals of the title compound, mp 122°-123° C.

EXAMPLE 3

6-chloro-2-(4-methyl-1-piperazinyl)-pyrazine hydrochloride

A mixture of 2,6-dichloropyrazine (12.5 g, 92% pure; 0.077 mole) and N-methylpiperazine (16.5 g, 0.165 mole) in acetonitrile (100 ml) is refluxed 18 hours under N₂. The mixture is concentrated in vacuo and partitioned between chloroform and water. The chloroform extract is washed with two 25 ml portions of 2 N aqueous acetic acid and 25 ml water and the combined aqueous acetic acid extracts basified with sodium hydroxide. Extraction with chloroform gives a crude product which is chromatographed on silica gel. Elution with 1–2% methanol-chloroform gives the pure base which is converted to the title salt with anhydrous hydrogen chloride in 95% aqueous ethanol. The pure title salt is collected by suction and dried, mp 283.5°-284° C.

EXAMPLE 4

6-chloro-2-(4-acetyl-1-piperazinyl)-pyrazine

6-Chloro-2-(1-piperazinyl)-pyrazine hydrochloride (15 g, 0.064 mole) is added to a solution of 20 g of sodium acetate trihydrate (0.147 mole) in 250 ml ice water. The vigorously stirred mixture is treated with 15 ml acetic anhydride followed by 100 ml water. The mixture is stirred 3 hours while warming to room temperature and the product, which separates as an oil, is extracted with toluene. The toluene extract is washed with water and concentrated in vacuo to give a crude product which is recrystallized twice from n-butylchloride to give the title compound, mp 106°-107.5° C.

EXAMPLE 5

6-chloro-2-(4-benzoyl-1-piperazinyl)-pyrazine

Using a procedure similar to that of Example 4, 2.35 g (0.010 mole) of 6-chloro-2-(1-piperazinyl)-pyrazine hydrochloride is dissolved in 20 ml saturated aqueous sodium carbonate solution and treated with 2 ml benzoyl chloride. After stirring 10 minutes at room temperature, the crude product is extracted with toluene and recrystallized from n-butyl-chloride-cyclohexane (charcoal treatment) to give colorless crystals of the title compound, mp 104.5°-105° C.

EXAMPLE 6

6-chloro-2-[4-(2'-propaniminooxycarbonyl)-1-piperazinyl]-pyrazine

Using a procedure analogous to Example 4, 2.35 g (0.010 mole) 6-chloro-2-(1-piperazinyl)-pyrazine hydrochloride is dissolved in 20 ml saturated aqueous sodium carbonate and the stirred suspension treated with two 1.4 g portions of 2-propaniminooxycarbonyl chloride with cooling in an ice bath. After 30 minutes, the mixture is extracted with benzene and the combined benzene extracts chromatographed on silica gel. Elution with 0–1% methanol-chloroform gives fractions containing pure product which are concentrated in vacuo and the residue crystallized from n-butylchloride to give white prisms of the title compound, mp 128°–129° C.

EXAMPLE 7

6-chloro-2-(4-cyclopropyl-1-piperazinyl)-pyrazine hydrochloride

Crude N-cyclopropylpiperazine (2.8 g) and 2,6-dichloropyrazine (3.0 g) are combined in 5 ml 2,2,2-trifluoroethanol and the mixture refluxed 4 hours under $N_2$. The mixture is concentrated under vacuum and the residue partitioned between aqueous sodium carbonate and methylene chloride. The combined methylene chloride extracts are extracted with dilute hydrochloric acid which is made basic with sodium hydroxide. The crude base is extracted with methylene chloride and chromatographed on silica gel. Elution with $CHCl_3$ gives fractions containing 2.4 g pure title base which is treated with hydrogen chloride in ethanol-isopropanol to give 2.0 g of the title salt, mp greater than 340° C. with decomposition at 245° C.

EXAMPLE 8

6-chloro-2-(4-cyclopropylmethyl-1-piperazinyl)-pyrazine hydrochloride

To a stirred suspension of 4.70 g (20.0 mmol) of 6-chloro-2-(1-piperazinyl)-pyrazine hydrochloride in 75 ml saturated aqueous sodium carbonate cooled in an ice bath is added 3 ml (33 mmol) of cyclopropanecarboxylic acid chloride. The mixture is stirred 45 minutes at ice bath temperature and then treated with 5 ml methylene chloride and warmed to room temperature during 30 minutes. Additional acid chloride (3 ml, 33 mmol) is added and stirring is continued 30 minutes longer. The mixture is diluted with water and extracted with chloroform to give 5 g crude 6-chloro-2-(4-cyclopropanecarbonyl-1-piperazinyl)-pyrazine which crystallizes, mp 69°–71° C. (100%).

To a stirred slurry of 3.0 g (11 mmol) of the product from the previous step in 30 ml dry ether is added 5.5 ml of a 70% benzene solution of sodium bis-2-methoxyethoxyaluminum hydride at −20° C. under $N_2$. The temperature of the mixture is raised to +10° C. for 20 minutes and the mixture is recooled to −20° C. and treated dropwise with 33 ml 4 N aqueous hydrochloric acid. The aqueous acid layer is extracted with chloroform, adjusted to pH8 with sodium bicarbonate and the crude title base extracted with chloroform and chromatographed on silica gel. Elution with ethylacetate-chloroform gives fractions containing 0.8 g (29%) of pure title base which is converted to the hydrochloride, mp 254° C. dec in ethanol-isopropanol containing hydrochloric acid.

EXAMPLE 9

6-chloro2-(4-allyl-1-piperazinyl)-pyrazine hydrochloride

A stirred suspension of 6-chloro-2-(1-piperazinyl)-pyrazine hydrochloride (2.35 g, 10.0 mmol) and 2.8 g potassium carbonate in 25 ml of acetonitrile at 50° C. is treated with 0.9 ml (10.4 mmol) allylbromide. After 4 hours at 50° C. the mixture is concentrated under vacuum and the residue partitioned between water and chloroform. The chloroform extract is chromatographed on silica gel. Elution with 1% methanol-chloroform gives fractions containing 0.4 g (15%) title salt, mp 233.5°–234° C. by treatment with hydrogen chloride in ethanol-isopropanol.

EXAMPLE 10

Preparation of Capsule Formulation

| Ingredient | Milligrams per Capsule |
| --- | --- |
| 6-chloro-2-(4-methyl-1-piperazinyl)-pyrazine | 6 |
| Starch | 87 |
| Magnesium stearate | 7 |

The active ingredient, starch and magnesium stearate are blended together. The mixture is used to fill hard shell capsules of a suitable size at a weight of 100 milligrams per capsule.

EXAMPLE 11

| | Milligrams per |
| --- | --- |
| 6-chloro-2-(4-benzoyl-1-piperazinyl)-pyrazine | 12 |
| Lactose | 200 |
| Corn Starch (for mix) | 50 |
| Corn Starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° C. The dry granules are passed through a No. 16 screen. The mixture is lubricated with magnesium stearate and compressed into tables in a suitable tableting machine. Each tablet contains 12 milligrams of active ingredient.

We claim:

1. A compound of the formula:

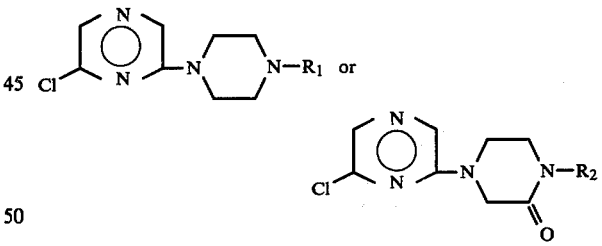

wherein $R_1$ is allyl, cyclopropyl, cyclopropylalkyl of 4–6 carbon atoms or propaniminooxycarbonyl and $R_2$ is alkyl of 1–4 carbon atoms and the pharmaceutically acceptable salts thereof.

2. A compound as in claim 1 wherein the compound is 6-chloro-2-(4-allyl-1-piperazinyl)-pyrazine.

3. A compound as in claim 1 wherein the compound is 6-chloro-2-(4-cyclopropyl-1-piperazinyl)-pyrazine.

4. A compound as in claim 1 wherein the compound is 6-chloro-2-(4-cyclopropylmethyl-1-piperazinyl)-pyrazine.

5. A compound as in claim 1 wherein the compound is 6-chloro-2-[4-(2′-propaniminooxycarbonyl)-1-piperazinyl]-pyrazine.

6. A compound as in claim 1 wherein the compound is 6-chloro-2-(4-methyl-3-oxo-1-piperazinyl)-pyrazine.

* * * * *